United States Patent [19]

Wade

[11] Patent Number: 4,591,588

[45] Date of Patent: May 27, 1986

[54] TRIAZOLO[1,5-C]PYRIMIDINES AND BRONCHODILATION USE THEREOF

[75] Inventor: James J. Wade, Oakdale, Minn.

[73] Assignee: Riker Laboratories, Inc., St. Paul, Minn.

[21] Appl. No.: 583,386

[22] Filed: Feb. 24, 1984

[51] Int. Cl.[4] ..................... A61K 31/54; C07D 487/04
[52] U.S. Cl. .................................... 514/222; 544/58.2
[58] Field of Search ....................... 544/58.2; 424/246; 514/222

[56] References Cited

U.S. PATENT DOCUMENTS 4,269,980  5/1981  Hardy, Jr. et al. ................ 544/256

FOREIGN PATENT DOCUMENTS

| 1205144 | 6/1957 | France. |
| 859287 | 1/1961 | United Kingdom. |
| 873223 | 7/1961 | United Kingdom. |
| 897870 | 5/1962 | United Kingdom. |
| 898409 | 6/1962 | United Kingdom. |

OTHER PUBLICATIONS

G. W. Miller et al., *J. Chem. Soc.*, 1963, 5642.
G. W. Miller et al., *J. Chem. Soc.*, 1965, 3357.
W. Broadbent et al., *J. Chem. Soc.*, 1965, 3369.
Temple et al., *J. Org. Chem.*, 1967, 33, 530.
D. J. Brown et al., *Aust. J. Chem.*, 1978, 31, 2505.
D. J. Brown et al., *Aust. J. Chem.*, 1979, 32, 1585.
D. J. Brown et al., *Aust. J. Chem.*, 1980, 33, 1147.

*Primary Examiner*—Richard L. Raymond
*Attorney, Agent, or Firm*—Donald M. Sell; James A. Smith; Robert W. Sprague

[57] ABSTRACT

1,2,4-Triazolo[1,5-c]pyrimidines substituted at the 7 position through a nitrogen atom which is part of a 1-oxo- or 1,1-dioxothiomorpholine ring have been found to have potent bronchodilator activity. Pharmacological methods of using these compounds and pharmaceutical compositions containing these compounds are also disclosed.

6 Claims, No Drawings

TRIAZOLO[1,5-c]PYRIMIDINES AND BRONCHODILATION USE THEREOF

TECHNICAL FIELD

The present invention relates to triazolo[1,5-c]pyrimidines, and more specifically to 1,2,4-triazolo[1,5-c]pyrimidines. The pharmacological use of the compounds of the invention as bronchodilators and pharmaceutical compositions comprising the compounds are also within the scope of the invention.

BACKGROUND OF THE INVENTION

Some 1,2,4-triazolo[1,5-c]pyrimidines are known to the art. Certain 1,2,4-triazolo[1,5-c]pyrimidines are disclosed as being bronchodilators in the patents discussed below, the compounds being referred to therein as triazolo[2,3-c]pyrimidines:

United Kingdom Pat. No. 859,287 discloses 2-amino-1,2,4-triazolo[1,5-c]pyrimidines which are substituted on the pyrimidine ring at the 5, 7 and 8 positions by certain combinations of substituents selected from hydrogen, alkyl, halogen-substituted alkyl, hydroxy-substituted alkyl, alkoxy-substituted alkyl, alkenyl, cycloalkyl, amino, alkylamino, dialkylamino, phenyl, alkylthio, alkoxy and halogen substituents. United Kingdom Pat. No. 898,409 discloses processes for preparing certain of these compounds by subjecting the corresponding 1,2,4-triazolo[4,3-c]pyrimidines to an acid treatment, to an alkaline treatment, or to a heat treatment.

United Kingdom Pat. No. 873,223 discloses 2-amino or 2-acetamido-1,2,4-triazolo[1,5-c]pyrimidines which are substituted on the pyrimidine ring at the 5, 7 and 8 positions by certain combinations of substituents selected from hydrogen, alkyl, halogen-substituted alkyl, alkoxy-substituted alkyl, alkenyl, cycloalkyl, alkylthio and halogen substituents.

United Kingdom Pat. No. 897,870 discloses 2-alkylamino-1,2,4-triazolo[1,5-c]pyrimidines, 2-dialkylamino-1,2,4-triazolo[1,5-c]pyrimidines, and 1,2,4-triazolo[1,5-c]pyrimidines containing a piperidino or morpholino substituent bonded at the 2-position through the nitrogen atom, which compounds are substituted on the pyrimidine ring at the 5, 7 and 8 positions by certain combinations of substituents selected from hydrogen, alkyl, halogen-substituted alkyl, hydroxy-substituted alkyl, alkenyl and halogen substituents.

The following related articles disclose the synthesis of certain 1,2,4-triazolo[1,5-c]pyrimidines as potential bronchodilators:

G. W. Miller et al., *J. Chem. Soc.*, 1963, 5642, discloses 2-amino- or 2-acetamido-1,2,4-triazolo[1,5-c]pyrimidines (referred to therein as triazolo[2,3-c]pyrimidines) which are substituted on the pyrimidine ring by, for example, hydrogen and alkyl substituents. Certain of these compounds are said to be bronchodilators.

G. W. Miller et al., *J. Chem. Soc.*, 1963, 3357, discloses 1,2,4-triazolo[1,5-c]pyrimidines (referred to therein as triazolo[2,3-c]pyrimidines) which are substituted at the 2-position by hydroxy, halogen, alkoxy, amino or substituted amino substituents and on the pyrimidine ring by alkyl substituents, or alkyl and halogen-substituted alkyl substituents.

W. Broadbent et al., *J. Chem. Soc.*, 1963, 3369, discloses 1,2,4-triazolo[1,5-c]pyrimidines (referred to therein as triazolo[2,3-c]pyrimidines) which are substituted at the 2-position by a mercapto, alkylthio, alkyl-sulphonyl, or dialkylamino substituent, and on the pyrimidine ring by alkyl substituents or alkyl and halogen-substituted alkyl substituents.

Still other 1,2,4-triazolo[1,5-c]pyrimidines are disclosed in the following articles and patents.

Temple et al., *J. Org. Chem.*, 1963, 33, 530, discloses the compound 8-amino-7-chloro-s-triazolo[1,5-c]pyrimidine-2(3H)-one.

D. J. Brown et al., *Aust. J. Chem.*, 1978, 31, 2505, discloses 1,2,4-triazolo[1,5-c]pyrimidines which are substituted at the 2-position by hydrogen or an alkyl substitutent, and on the pyrimidine ring by hydrogen and/or alkyl substituents.

D. J. Brown et al., *Aust. J. Chem.*, 1979, 32, 1585, discloses 1,2,4-triazolo[1,5-c]pyrimidines which are substituted at the 2-position by hydrogen or an alkyl substituent, and on the pyrimidine ring at the 5-position by a halogen, hydrazino, alkyl or alkylthio substituent, and at the 7-position by an alkyl substituent.

D. J. Brown et al., *Aust. J. Chem.*, 1980, 33, 1147, discloses pyrimidines which are substituted at the 2-position by hydrogen or an alkyl or phenyl substituent, and on the pyrimidine ring at the 5-position by halogen, dimethylaminomethyleneamino, hydroxyaminomethyleneamino or 5-acetoxyaminomethyleneamino, and at the 7-position by hydrogen or an alkyl substituent.

U.S. Pat. No. 4,269,980 discloses 5-, 7- and 8-(optionally substituted phenyl)-1,2,4-triazolo[1,5-c]pyrimidines. These compounds may be substituted at the 2-position by hydrogen or an alkyl substituent and are anxiolytic agents.

DETAILED DESCRIPTION OF THE INVENTION

The present invention relates to 1,2,4-triazolo[1,5-c]pyrimidines which are bronchodilators. The invention also relates to a method for including bronchodilation in a mammal using a 1,2,4-triazolo[1,5-c]pyrimidine of the invention, and to pharmaceutical compositions comprising an effective amount of a 1,2,4-triazolo[1,5-c]pyrimidine of the invention and a pharmaceutically acceptable carrier.

Specifically, the present invention relates to compounds of the formula I

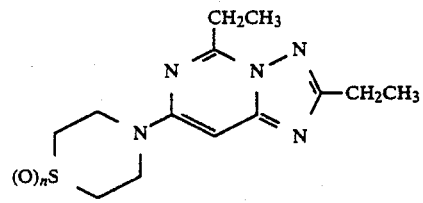

wherein n is 1 or 2; and pharmaceutically acceptable acid-addition salts thereof.

The compound of Formula I wherein n is 1 is named 2,5-diethyl-7-[4-(1-oxothiomorpholino)]-1,2,4-triazolo[1,5-c]pyrimidine, and the compound of Formula I wherein n is 2 is named 2,5-diethyl-7-[4-(1,1-dioxothiomorpholino)]-1,2,4-triazolo[1,5-c]pyrimidine.

The bronchodilator activity of the compounds of Formula I was assessed by the measurement of effects on isolated tracheal spirals. This is a well-known and long established in vitro test method. The bronchodilator activity was determined according to the following procedure: Female guinea pigs were sacrificed and each trachea removed and cut into a spiral strip. This strip was mounted in a constant temperature (37° C.) muscle bath having a volume of approximately 15 ml. The bathing medium was Krebs-Henseleit solution. Movement of the tracheal strip was measured by means of an isometric transducer connected to an electric recorder. The bath was aerated with a mixture of 95% carbon dioxide and 5% oxygen. Contractions were induced in the strips by the addition of a suitable amount of histamine, acetylcholine or barium chloride. The amount of a given compound of Formula I (measured in ug/ml) required to provide greater than 75% relaxation of drug-induced contraction is considered an effective concentration. For comparison, a well known standard bronchodilator, aminophylline, requires concentrations of 50 ug/ml versus histamine, 100 ug/ml versus acetylcholine and 10 ug/ml versus barium chloride to provide greater than 75% relaxation.

Both of the compounds of Formula I were active in the in vitro test, and were tested in vivo in the quinea pig for oral activity in the so-called histamine aerosol method described in U.S. Pat. No. 3,248,292. This test was modified slightly in that a 0.1% aqueous solution of histamine was used as the agent for inducing bronchial constriction. Oral doses were measured in mg/kg of body weight of the guinea pig.

The compounds of Formula I may be administered to mammals in order to obtain bronchodilation. The compounds may be administered orally, parenterally or by inhalation. Preferably they are administered orally in tablets or capsules. The usual effective human dose will be in the range of 0.1 to 5 mg/kg of body weight.

Salts of compounds of Formula I are generally prepared by reaction with an equimolar amount of a relatively strong acid, preferably an inorganic acid such as hydrochloric, sulfuric or phosphoric acid, in a polar solvent. Isolation of the salt is facilitated by the addition of a solvent in which the salt is insoluble, an example of such a solvent is diethyl ether.

The compounds of Formula I, either as the free base or in the form of a pharmaceutically acceptable acid-addition salt, can be combined with conventional pharmaceutical diluents and carriers to form such dosage forms as tablets, capsules, suspensions, solutions, suppositories and the like.

The pharmaceutical carrier employed may be, for example, either a solid or liquid. Examples of solid carriers are lactose, terra alba, sucrose, talc, gelatin, agar, pectin, acacia, magnesium stearate, stearic acid, and the like. Liquid carriers include syrup, peanut oil, olive oil, water and the like. Similarly, the carrier or diluent can include a time delay material well known to the art, such as glyceryl monostearate or glyceryl distearate, these being employed alone or, for example, in combination with a wax.

The compounds of Formula I may be prepared by several synthetic routes. One such route is that shown in Scheme I below wherein n is as defined above, and each alk is independently an alkyl group containing 1 to about 4 carbon atoms.

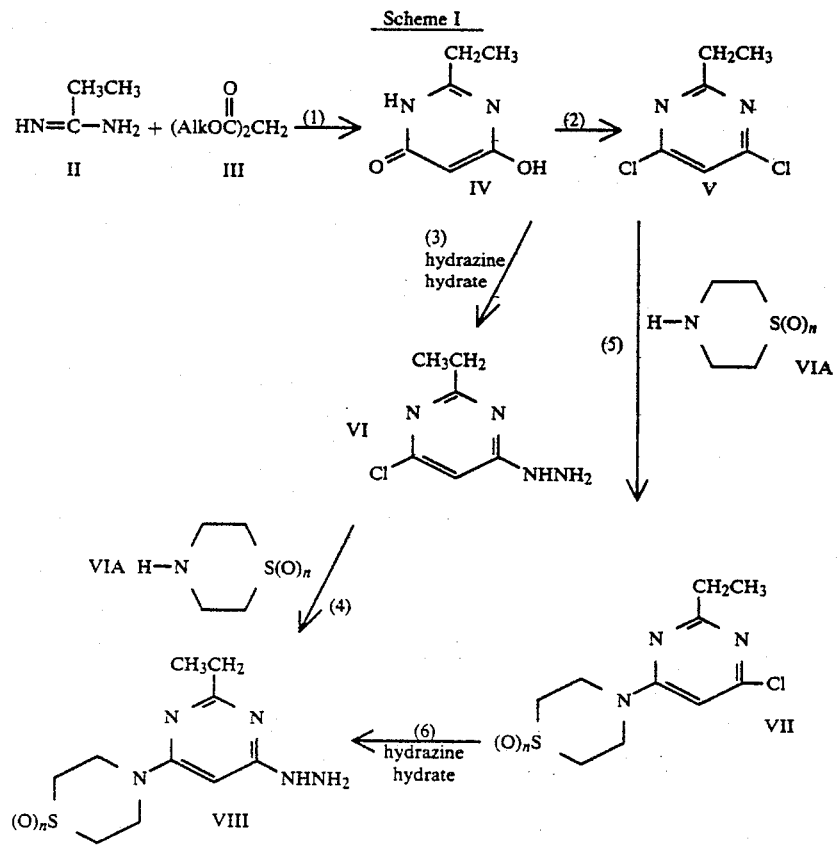

Scheme I -continued

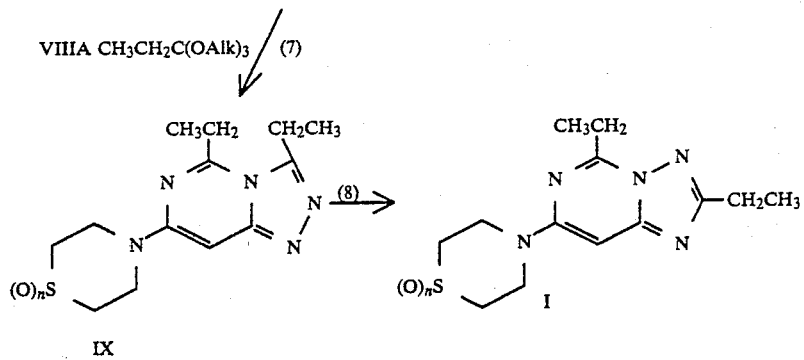

The reactions of steps (1), (2) and (3) have previously been reported. Thus compounds of formulas IV, V, and VI are known. The known methods were used to carry out the reactions of steps (1), (2) and (3). Specifically, steps (1) and (2) were carried out as described in H. R. Henze et al., *J. Org. Chem.*, 1952, 17, 1320 and H. R. Henze et al., *J. Org. Chem.*, 1953, 18, 653, and step (3) was carried out as described in J. Chesterfield et al., *J. Chem. Soc.*, 1955, 3478. Propionamidine acetate, which may also be used as a starting material in step (1), can be prepared as described in Taylor et al., *J. Am. Chem. Soc.*, 1960, 82, 3138.

Step (4) is carried out by reacting 4-chloro-2-ethyl-6-hydrazinopyrimidine of Formula VI with a heterocyclic amine of the formula VIA. The reactants are heated together without solvent or optionally (and preferably) in any solvent which does not participate in the reaction such as water. Two equivalents of the heterocyclic amine are preferably used. Alternatively, one equivalent of the heterocyclic amine may be replaced by an inorganic base to neutralize the hydrogen chloride, but lower yields are obtained. The reaction mixture is heated at a temperature up to or at its reflux temperature. A temperature is chosen which provides an adequate reaction rate. When water is used as the solvent, the temperature is generally in the range of 80° to 110° C. Good yields of the desired products are isolated by conventional methods such as filtration, extraction or chromatography. The novel intermediate of Formula VIII, which may also be prepared alternatively by following steps (5) and (6), are solids whose structural assignments are confirmed by infrared and nuclear magnetic resonance spectral analyses.

Step (5) is carried out by reacting 2-ethyl-4,6-dichloropyrimidine of Formula V with heterocyclic amines of the formula VIA. This reaction is carried out by heating the reactants without solvent, or preferably in any solvent which does not participate in the reaction. Two equivalents of the heterocyclic amine are preferably used, one to react with the chloropyrimidine and the other to neutralize the hydrogen chloride by-product. Alternatively, an inorganic base may be used to neutralize the hydrogen chloride by-product, but lower yields of the desired product are generally obtained. Heating is at a temperature up to and including the reflux temperature of the mixture. A temperature is chosen which provides an adequate reaction rate. If water is used as a solvent, the mixture is generally heated at its reflux temperature. Good yields of the desired product are isolated by conventional methods such as filtration, extraction or chromatography. The novel intermediates of Formula VII are solids. Structural assignments are confirmed by infrared and nuclear magnetic resonance spectral analyses.

Step (6) is carried out by reacting the novel substituted 4-chloro-2-ethyl-6-heterocyclicaminopyrimidine of Formula VII with hydrazine hydrate. The reaction is facile and is generally carried out at moderate temperatures, for example, from −20° C. to the reflux temperature of the solvent. The reaction is generally carried out by adding two equivalents of hydrazine hydrate to a solution of the pyrimidine. The solvent will generally be a lower alkanol. The product is separated by conventional methods such as filtration, extraction or chromatography and is the same novel intermediate of Formula VIII obtained from step (4).

Step (7) is carried out by reacting the intermediate of Formula VIII with an orthoester of formula VIIIA. Such orthoesters are well known and readily available. Examples of suitable orthoesters include trimethyl orthopropionate, triethyl orthopropionate and the like. Since the orthoesters are liquids, it is convenient to mix the intermediates of Formula VIII with an excess of orthester and to heat the mixture at reflux until reaction is complete. Good yields of the desired solid, novel intermediates of Formula IX which are novel substituted 1,2,4-triazolo[4,3-c]pyrimidines are obtained by conventional methods.

In step (8), the 1,2,4-triazolo[4,3-c]pyrimidines of Formula IX are heated with an aqueous alkanoic acid such as formic acid, acetic acid or propionic acid and thereby converted to the desired compounds of the invention of Formula I. The reaction mixture is generally heated at reflux for up to several days.

Alternatively, step (8) may be conducted by heating the compound of Formula IX in the presence of a strong base such as a metal alkoxide, for example, sodium methoxide.

The desired product of step (8) is isolated by conventional methods. The structural assignments are made based on infrared and nuclear magnetic resonance spectral analyses. The products are generally white crystalline solids.

In some cases step (8) may be accomplished by continued heating of the reactants of step (7). This conversion occurs most readily by using dimethyl sulfoxide as the solvent for the combined steps (7) and (8).

Synthetic Scheme II shows a method for the preparation of compounds of Formula I starting with 2,5-diethyl-7-(4-thiomorpholino)-1,2,4-triazolo[1,5-c]pyrimidine, which may be prepared using the method of Scheme I.

Scheme II

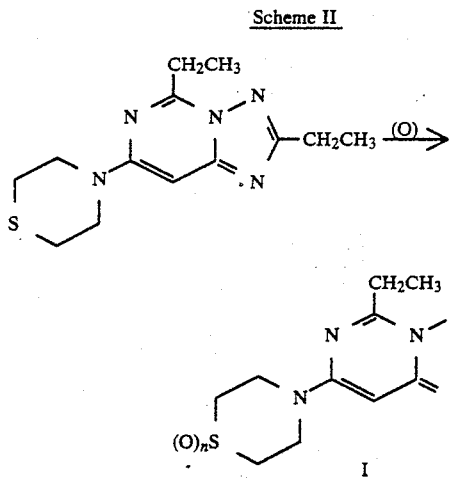

The oxidation reaction of Scheme II is readily carried out using equimolar amounts of known oxidizing agents by adding said oxidizing agents gradually in solution. Under such procedures the reaction occurs to a large extent in stepwise fashion, providing first the sulfoxide ($n=1$) and then the sulfone ($n=2$).

Suitable oxidizing agents are hydrogen peroxide, sodium metaperiodate, and peracids such as (preferably) meta-chloroperbenzoic acid, peracetic acid, pertrifluoroacetic acid, perbenzoic acid and the like. Any relatively mild oxidizing agent which will oxidize sulfur to sulfoxide or sulfoxide to sulfone could be used.

The reaction temperatures are generally moderate from $-20°$ C. to $30°$ C., although in some cases mild exotherms are noted.

Suitable solvents are those inert solvents which are stable to the reaction conditions such as aqueous ethanol, dichloromethane, chloroform and the like.

The following examples are provided to illustrate the methods used in the invention. They are not intended to limit the invention.

EXAMPLE 1

Preparation of 2,5-Diethyl-7-(4-thiomorpholino)-1,2,4-triazolo[1,5-c]pyrimidine

Step 1: Preparation of 2-Ethyl-4-hydrazino-6-(4-thiomorpholino)pyrimidine

Known 4,6-Dichloro-2-ethylpyrimidine (300.0 g, 1.695 moles) was dissolved in 2 l of methanol in a 5 l round bottom flask fitted with a mechanical stirrer, a thermometer, and an addition funnel, the flask then being placed in an ice bath cooled to $0°-5°$ C. Hydrazine hydrate (175.0 g, 3.50 moles) was added dropwise over 1 hour, keeping the temperature of the mixture less than or equal to $10°$ C. When the addition was complete, the mixture was first stirred at $0°-10°$ C. for 30 minutes, and was then stirred at ambient temperature (about $20°$ C.) for 2 hours. The solids were recovered by filtration, and the filtrate was concentrated by rotary evaporation. The resulting white solid was combined with the white solid recovered by filtration, and the combined solid was slurried with water (about 1 l), filtered and washed with water. This water-wet solid was suspended in 3 l of water in a 5 l round bottom flask fitted with a mechanical stirrer and a reflux condenser. Thiomorpholine (361.0 g, 3.50 moles) was added, and the mixture was refluxed for 48 hours and then allowed to cool overnight. The solid was isolated by filtration, washed with water, and dried at $65°$ C. in vacuo to provide 384.1 g (1.61 moles, 94.7% yield) of the desired intermediate.

Step 2: Preparation of 3,5-Diethyl-7-(4-thiomorpholino)-1,2,4-triazolo[4,3-c]pyrimidine The intermediate from step 1 (354.0 g, 1.48 moles) and triethyl orthopropionate (650 g, 3.69 moles) were refluxed for 24 hours. The reaction flask was then fitted with a distillation head, and 250 ml of ethanol, boiling at $73°-81°$ C., was removed from the reaction mixture by distillation. The reaction mixture was refluxed for an additional 48 hours, and then allowed to cool overnight at $-10°$ C., precipitating a yellow solid. This solid was collected by filtration, washed with diethyl ether, and dried at $60°$ in vacuo to provide 358.6 g (1.29 moles, 87.4% yield) of the desired intermediate as an off-white solid.

Step 3: Preparation of 2,5-Diethyl-7-(4-thiomorpholino)-1,2,4-triazolo[1,5-]pyrimidine 3,5-Diethyl-7-(4-thiomorpholino)-1,2,4-triazolo[4,3-c]pyrimidine (375.0 g, 1.35 moles) was refluxed for 5 hours in 1 l of 95% formic acid. The reaction mixture was concentrated by rotary evaporation and the residue poured onto ice. The resulting solution was made basic with concentrated ammonium hydroxide, thereby precipitating a thick solid. This solid was isolated by filtration, washed well with water, and dried at $85°$ in vacuo. This material, amounting to 314.7 g (1.13 moles, 84.1% yield), was recrystallized with treatment with decolorizing charcoal from cyclohexane (about 8 l) to give 221.7 g (0.799 moles, 59.2% yield) of white solid. A second and a third crop were obtained by concentrating the mother liquors and recrystallizing the residue from cyclohexane, providing an additional 74.8 g of white solid. The total yield was 296.5 g (1.07 moles, 79.1% yield) of solid which was determined to be pure by thin layer chromatography and nuclear magnetic resonance spectroscopy.

EXAMPLE 2

Preparation of 2,5-Diethyl-7-[4-(1,1-dioxothiomorpholino)]-1,2,4-triazolo[1,5-c]pyrimidine and Bisulfate salt thereof To a stirred solution of 5.5 g (20 mmoles) of 2,5-diethyl-7-(4-thiomorpholino)-1,2,4-triazolo[1,5-c]pyrimidine in 100 ml of chloroform was added, dropwise over 3.5 hours, 8.6 g (50 mmoles) of meta-chloroperbenzoic acid in 100 ml of chloroform. The mixture was stirred for an additional 16 hours. Thin layer chromatography showed incomplete reaction. An additional 1.5 g of meta-chloroperbenzoic acid was dissolved in 25 ml of chloroform, and the solution was added dropwise over 45 minutes. The mixture was stirred for one additional hour. Thin layer chromatography showed that the reaction had progressed but was still incomplete. An additional 1.5 g of meta-chloroperbenzoic acid was dissolved in 25 ml of chloroform and the solution was added dropwise over 45 minutes. After stirring the mixture for about 90 hours, it was washed thrice with 10% aqueous sodium hydroxide solution, and then with water and saturated sodium chloride solution. Drying over magnesium sulfate and evaporation of the solvent provided a white solid which was recrystallized from ethyl acetate. The solid product was separated by filtration and found by thin layer chromatography to be primarily the desired product. A second crop was obtained by adding cyclohexane to the ethyl acetate filtrate. The white solid second crop was collected by filtration and determined by thin layer chromatography to be pure 2,5-diethyl-7-[4-(1,1-dioxothiomorpholino)]-1,2,4-triazolo[1,5-c]pyrimidine, m.p. 187°–189° C. Analysis: Calculated for $C_{13}H_{19}N_5O_2S$: %C, 50.5; %H, 6.2; %N, 22.6; Found: %C, 50.3; %H, 6.1; %N, 23.0.

To a warm solution of 1.0 g (3.2 mmole) of 2,5-diethyl-7-[4-(1,1-dioxothiomorpholino)]-1,2,4-triazolo[1,5-c]pyrimidine in 50 ml of ethanol was added dropwise 0.30 g (3.1 mmole) of concentrated sulfuric acid. The solution was stirred and allowed to cool to about 20° C., then diluted to a total volume of 300 ml with diethyl ether. After stirring for one hour, the solid was collected by filtration, rinsed with ether and dried to provide 2,5-diethyl-7-[4-(1,1-dioxothiomorpholino)]-1,2,4-triazolo[1,5-c]pyrimidine bisulfate, m.p. 189°–191° C. Analysis: Calculated for $C_{13}H_{19}N_5O_2S.H_2SO_4$: %C, 38.3; %H, 5.2; %N, 17.2; Found: %C, 38.5; %H, 5.2; %N, 17.6.

EXAMPLE 3

Preparation of 2,5-Diethyl-7-[4-(1-oxothiomorpholino)]-1,2,4-triazolo[1,5-c]pyrimidine and Bisulfate salt thereof To a stirred solution of 8.3 g (30 mmoles) of 2,5-diethyl-7-(4-thiomorpholino)-1,2,4-triazolo[1,5-c]pyrimidine in 75 ml of chloroform was added, dropwise over 35 minutes, 80 ml of a chloroform solution of 5.2 g (30 mmoles) of meta-chloroperbenzoic acid. A mild exotherm was observed, and the solution was stirred for an additional 45 minutes. Thin layer chromatography showed incomplete reaction. An additional 0.5 g of meta-chloroperbenzoic acid was dissolved in 10 ml of chloroform, and the solution was added dropwise to the reaction mixture. After stirring for an additional 1.5 hours, the reaction mixture was washed sequentially with 10% sodium hydroxide solution, water and saturated sodium chloride solution, and was then dried over magnesium sulfate. The dried organic layer was then evaporated to provide an off-white solid residue. Chromatography on silica gel, eluting with 1:9 methanol-chloroform, provided starting material in early fractions and product in later fractions. The product was white solid 2,5-diethyl-7-[4-(1-oxothiomorpholino)]-1,2,4-[1,5-c]pyrimidine, m.p. 223°–225° C. The structure was confirmed by $C^{13}$ nuclear magnetic resonance and infrared spectral analyses. Analysis: Calculated for $C_{13}H_{19}N_5OS$: %C, 53.2; %H, 6.5; %N, 23.9; Found: %C, 53.1% %H, 6.4; %N, 23.8.

To a warm solution of 2.5 g (8.5 mmoles) of 2,5-diethyl-7-[4-(1oxothiomorpholino)]-1,2-4-triazolo[1,5-c]pyrimidine in 60 ml of ethanol was added dropwise 0.82 g (8.4 mmoles) of concentrated sulfuric acid. The solution was allowed to cool to about 20° C., then diluted to a total volume of 250 ml by the addition of diethyl ether. The mixture was stirred for one hour, and the solid was then separated by filtration. The solid was washed with ether and dried to provide white solid 2,5-diethyl-7-[4-(1-oxothiomorpholino)]-1,2,4-triazolo[1,5-c]pyrimidine bisulfate, m.p. 210°–212° C. Analysis: Calculated for $C_{13}H_{19}N_5OS.H_2SO_4$: %C, 39.9; %H, 5.4; %N, 17.9; Found; %C, 39.9; %H, 5.4; %N, 18.2.

EXAMPLE 4

Alternative preparation of 2,5-Diethyl-7-[4-(1,1-dioxothiomorpholino)]-1,2,4-triazolo[1,5-c]pyrimidine Part A: Preparation of 4-Chloro-6-[4-(1,1-dioxothiomorpholino)]-2-ethylpyrimidine To a solution of 5.4 g (40 mmole) of 1,1-dioxothiomorpholine in 100 ml of water was added 3.5 g (20 mmole) of 4,6-dichloro-2-ethylpyrimidine. The mixture was heated at its reflux temperature for one day and chilled. The white solid was collected, washed with water and dried to provide 4-chloro-6-[4-(1,1-dioxothiomorpholino)]-2-ethylpyrimidine, m.p. (crude) 164°–172° C. Thin layer chromatography analysis on silica gel, eluting with 1:9 methanol:chloroform, showed one component. The structural assignment was confirmed by nuclear magnetic resonance spectral analysis.

Part B: Preparation of 6-[4-(1,1-dioxothiomorpholino)]-2-ethyl-4-hydrazinylpyrimidine To a suspension of 4.6 g (17 mmole) of 4-chloro-6-[4-(1,1-dioxothiomorpholino)]-2-ethylpyrimidine in 75 ml of methanol was added 1.7 g (34 mmole) of hydrazine hydrate. The mixture was heated at its reflux temperature for 2 days. Evaporation provided a residue which was washed thoroughly with water and examined by thin layer chromatography. The residue was about two-thirds starting material. The residue was suspended in 75 ml of methanol, 1.7 g of hydrazine hydrate was added and the mixture was heated at reflux for one week. The mixture was cooled, and was then evaporated to provide a residue. The residue was washed by stirring with 100 ml of water, separated by filtration, washed with water and dried to provide tan solid 6-[4-(1,1-dioxothiomorpholino)]-2-ethyl-4-hydrazinylpyrimidine, m.p. (crude) 158°–166° C. The structural assignment was confirmed by infrared and nuclear magnetic resonance spectral analyses.

Part C: Preparation of 3,5-Diethyl-7-[4-(1,1-dioxothiomorpholino)]-1,2,4-triazolo[4,3-c]pyrimidine A suspension of 1.5 g (5.5 mmole) of 6-[4-(1,1-dioxothiomorpholino)]-2-ethyl-4-hydrazinylpyrimidine in 35 ml of triethyl orthopropionate was heated at its reflux temperature for four days, then cooled at about 0° C. for about 16 hours. The solid was collected by filtration, washed with diethyl ether and dried to provide light brown solid 3,5-diethyl-7-[4-(1,1-dioxothiomorpholino)]-1,2,4-triazolo[4,3-c]pyrimidine, m.p. (crude) 193°–199° C. Thin layer chromatography on silica gel eluting with 1:9 methanol:chloroform showed one product. The structural assignment was confirmed by nuclear magnetic resonance spectral analysis.

Part D: Preparation of 2,5-Diethyl-7-[4-(1,1-dioxothiomorpholino)]-1,2,4-triazolo[1,5-c]pyrimidine A mixture of 0.6 g (1.9 mmole) of 3,5-diethyl-7-[4-(1,1-dioxothiomorpholino)]-1,2,4-triazolo[4,3-c]pyrimidine and 25 ml of formic acid was heated at its reflux temperature for one day. The mixture was evaporated to dryness and the residue combined with an ice-water mixture. The mixture was basified with concentrated ammonium hydroxide. The solid was collected by filtration, washed twice with water and dried to provide as a light brown solid 2,5-diethyl-7-[4-(1,1-dioxothiomorpholino)]-1,2,4-triazolo[1,5-c]pyrimidine, m.p. 182°-185° C. This compares to the melting point of pure product from the previous Example 2 of 187°-189° C. The product of the present Example was found to be the same as the product of Example 2 by comparison of infrared and nuclear magnetic resonance spectra and by thin layer chromatography.

EXAMPLE 5

Preparation of 4-Chloro-2-ethyl-6-[4-(1-oxothiomorpholino)]pyrimidine

To a solution of 7.9 g (66 mmole) of 1-oxothiomorpholine in 150 ml of water was added 5.8 g (33 mmole) of 4,6-dichloro-2-ethylpyrimidine. The mixture was heated at its reflux temperature for 29 hours, then stirred at 20° C. for 16 hours. The mixture was stirred and chilled in an ice bath, and the solid was then collected by filtration. The solid was dissolved in chloroform, and the solution was washed with water, dried over magnesium sulfate, and evaporated. The residue was a white solid which was found by thin layer chromatography on silica gel, eluting with 1:9 methanol:chloroform, to be chiefly the desired product, 4-chloro-2-ethyl-6-[4-(1-oxothiomorpholino)]pyrimidine and some starting material. The product is separable by chromatography.

EXAMPLE 6

Using the method of Example 4, Parts A, B, C and D, and starting with 4,6-dichloro-2-ethylpyrimidine and 1-oxothiomorpholine, 2,5-diethyl-7-[4-(1-oxothiomorpholino)]-1,2,4-triazolo[1,5-c]pyrimidine could be obtained.

EXAMPLE 7

To 1.0 ml of 25% sodium methoxide (0.011 mmole) in methanol was added 3.00 g (10.8 mmole) of 3,5-diethyl-7-(4-thiomorpholino)-1,2,4-triazolo[4,3-c]pyrimidine. The mixture was heated at reflux for 30 minutes, and was then evaporated in vacuo to a solid which was suspended in 75 ml of water and filtered. Recrystallization with treatment with decolorizing charcoal from cyclohexane gave as a white solid the desired product, 2,5-diethyl-7-(4-thiomorpholino)-1,2,4-triazolo[1,5-c]pyrimidine.

EXAMPLE 8

Alternative Preparation of 2,5-Diethyl-7-[4-(1,1-dioxothiomorpholino)]-1,2,4-triazolo[1,5-c]pyrimidine To a cold (0° C.) stirred solution of 5.12 g (18.5 mmoles) of 2,5-diethyl-7-(4-thiomorpholino)-1,2,4-triazolo[1,5-c]pyrimidine in 100 ml of chloroform was added, over about 2 minutes, 10.0 g (46.4 mmoles) of meta-chloroperbenzoic acid in 50 ml of chloroform. The mixture was stirred at 0° C. for two hours and one hour at about 20° C. Thin layer chromatography showed complete reaction. The mixture was diluted to 200 ml with chloroform, and was washed thrice with 100 ml of 5% aqueous sodium hydroxide solution, and then thrice with 100 ml of water. Drying over magnesium sulfate and evaporation of the solvent provided a solid which was determined by thin layer chromatography to be pure 2,5-diethyl-7-[4-(1,1-dioxothiomorpholino)]-1,2,4-triazolo[1,5-c]pyrimidine. The solid was chromatographed over silica gel, eluting with 10:90 acetone:ethyl acetate, and collecting twenty 100 ml fractions. Fractions 6-11 were combined and evaporated. The resulting product had a m.p. of 188°-189° C. after recrystallization from ethyl acetate.

EXAMPLE 9

Alternative preparation of 2,5-Diethyl-7-[4-(1-oxothiomorpholino)]-1,2,4-triazolo[1,5-c]pyrimidine To a cold (0° C.), stirred solution of 1.00 g (3.61 mmole) of 2,5-diethyl-7-(4-thiomorpholino)-1,2,4-triazolo[1,5-c]pyrimidine in 40 ml of ethanol and 10 ml of water was added 0.93 g (4.35 mmole) of sodium metaperiodate. After 1.5 hours the mixture was poured into 50 ml of an ice-water mixture, then extracted with four 50 ml portions of chloroform. The extracts were washed thrice with 50 ml portions of water, dried over magnesium sulfate and evaporated. The white solid was recrystallized from 1:3 chloroform:hexane to provide, from two crops, 0.84 g (79%) of white solid 2,5-diethyl-7-[4-(1-oxothiomorpholino)]-1,2,4-triazolo[1,5-c]pyrimidine, corresponding to the product of Example 3 according to thin layer chromatographic analysis, and having a m.p. of 222°-223° C. after recrystallization from 3:2 chloroform:ethyl acetate.

What is claimed is:

1. A compound of the formula:

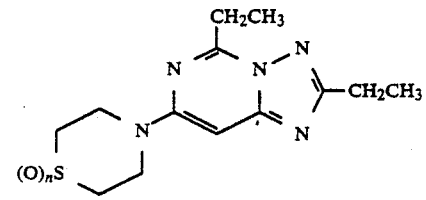

wherein n is 1 or 2; or a pharmaceutically acceptable acid-addition salt thereof.

2. A compound according to claim 1, wherein n is one.

3. A compound according to claim 1, wherein n is two.

4. A bronchodilator pharmaceutical composition comprising an effective amount of a compound according to claim 1 and a pharmaceutically acceptable vehicle.

5. A method for obtaining bronchodilation in a mammal, comprising administering an effective amount of a compound according to claim 1 to said mammal.

6. A method according to claim 6, wherein the compound is administered orally.

* * * * *